(12) United States Patent
Li et al.

(10) Patent No.: US 7,911,597 B2
(45) Date of Patent: Mar. 22, 2011

(54) INSPECTION APPARATUS TO SIMULTANEOUSLY MEASURE THE SUGAR CONTENT AND WEIGHT OF FRUIT

(75) Inventors: Wang-Sheng Li, Hsinwu (TW); Shui-Ho Cheng, Hsinwu (TW)

(73) Assignee: Taoyuan District Agricultural Research and Extension Station, Taoyuan County (TW)

( * ) Notice: Subject to any disclaimer, the term of this patent is extended or adjusted under 35 U.S.C. 154(b) by 0 days.

(21) Appl. No.: 11/984,884

(22) Filed: Nov. 23, 2007

(65) Prior Publication Data
US 2010/0214558 A1 Aug. 26, 2010

(51) Int. Cl.
*G01N 21/00* (2006.01)

(52) U.S. Cl. .......................... 356/72; 356/128

(58) Field of Classification Search .................. 356/51, 356/72, 128, 300, 601, 609, 625–628
See application file for complete search history.

(56) References Cited

U.S. PATENT DOCUMENTS
6,847,447 B2 * 1/2005 Ozanich .................. 356/326

FOREIGN PATENT DOCUMENTS
CN 101008611 * 8/2007
* cited by examiner

*Primary Examiner* — Tarifur Chowdhury
*Assistant Examiner* — Tara S Pajoohi
(74) *Attorney, Agent, or Firm* — Jackson IPG PLLC; Demian K. Jackson

(57) ABSTRACT

An inspection instrument includes main unit, Brix testing unit, weight measurement unit, display unit, control unit, and label printer; both of Brix and weight of an object pending test are tested and measured at the same time by the Brix testing unit and the weight measurement unit; resultant data are directly displayed on the inspection instrument by the display unit; data are directly printed on a label; and the label is outputted to be directly attached to the fruit.

7 Claims, 4 Drawing Sheets

INSPECTION APPARATUS TO SIMULTANEOUSLY MEASURE THE SUGAR CONTENT AND WEIGHT OF FRUIT

BACKGROUND OF THE INVENTION (a) Field of the Invention

The present invention is related to inspection instrument and more particularly, to one that tests Brix scale and measures weight of fruits.

(b) Description of the Prior Art

In Taiwan R&D results on the production of top quality fruits are very impressive, and significant achievements have been reported in species modifications, or in culture technology improvement; however, quality testing and measuring technologies commonly practiced by fruit growers today in Taiwan remain focusing on the ratings of size and appearance without analyzing those factors affecting internal quality of the fruits, namely, containment of compositions of quality, Brix, acidity, amino acid, and vitamins.

Furthermore, use of manual inspection of the exterior quality of agricultural products so to decide on ratings and selling prices not only consumes lengthy time, efforts, and high cost, but also fails to judge internal quality, e.g., Brix, of the agricultural products. As a result, there exists excessively great difference between the rating and the actual quality. Thought there are non-destructive on-line testing application systems for fruits generally available in the market, they are too expensive (e.g., one system may be sold at NT$40M up to NT$50M) and they get too complicated in measuring the Brix of fruits. First, the fruit must be put in a juicer before fetching a drop of the fruit juice with a burette to drop on a refractometer to determine the sugar containment (° Brix). Whereas those Brix testing instruments generally available in the market are related to destructive testing methods since the fruit must be first put into a juicer before conducting the Brix measurement, they are not applicable to the site where non-destructive Brix testing and rating, and thus their practicability is restricted. This warrants development of a summary non-destructive application system for testing quality of fruits.

SUMMARY OF THE INVENTION

The primary purpose of the present invention is to provide an inspection instrument to solve the problem found with the fruit Brix tester of the prior art that works only with destructive test to measure Brix of fruits.

Another purpose of the present invention is to provide an inspection instrument that immediately prints out the information of the measurement in a label and directly attaches the label on the fruit tested for achieving real time test and register.

Another purpose yet of the present invention is to provide an inspection instrument that tests the Brix, measures the weight, and displays the results at the same time.

To achieve these purposes, the present invention is comprised of a main unit, a Brix testing unit, a weight measurement unit, a display unit, a control unit, and a label printer. The main unit is related to a rigid enclosure and the Brix testing unit, the weight measurement unit, the display unit and the control unit are basically disposed on the main unit; the control unit is respectively linked to the Brix testing unit, the weight measurement unit, and the display unit; the label printer is adapted to one side of the main unit and also linked to the control unit. Accordingly, both of the Brix testing unit and the weight measurement unit measure the Brix and the weight at the same time with the resultant numeric values being directly displayed on the inspection instrument and then directly printed on a label through the label printer; the label is outputted and directly attached to the fruit tested.

DETAILED DESCRIPTION OF THE PREFERRED EMBODIMENTS

Figure 1:
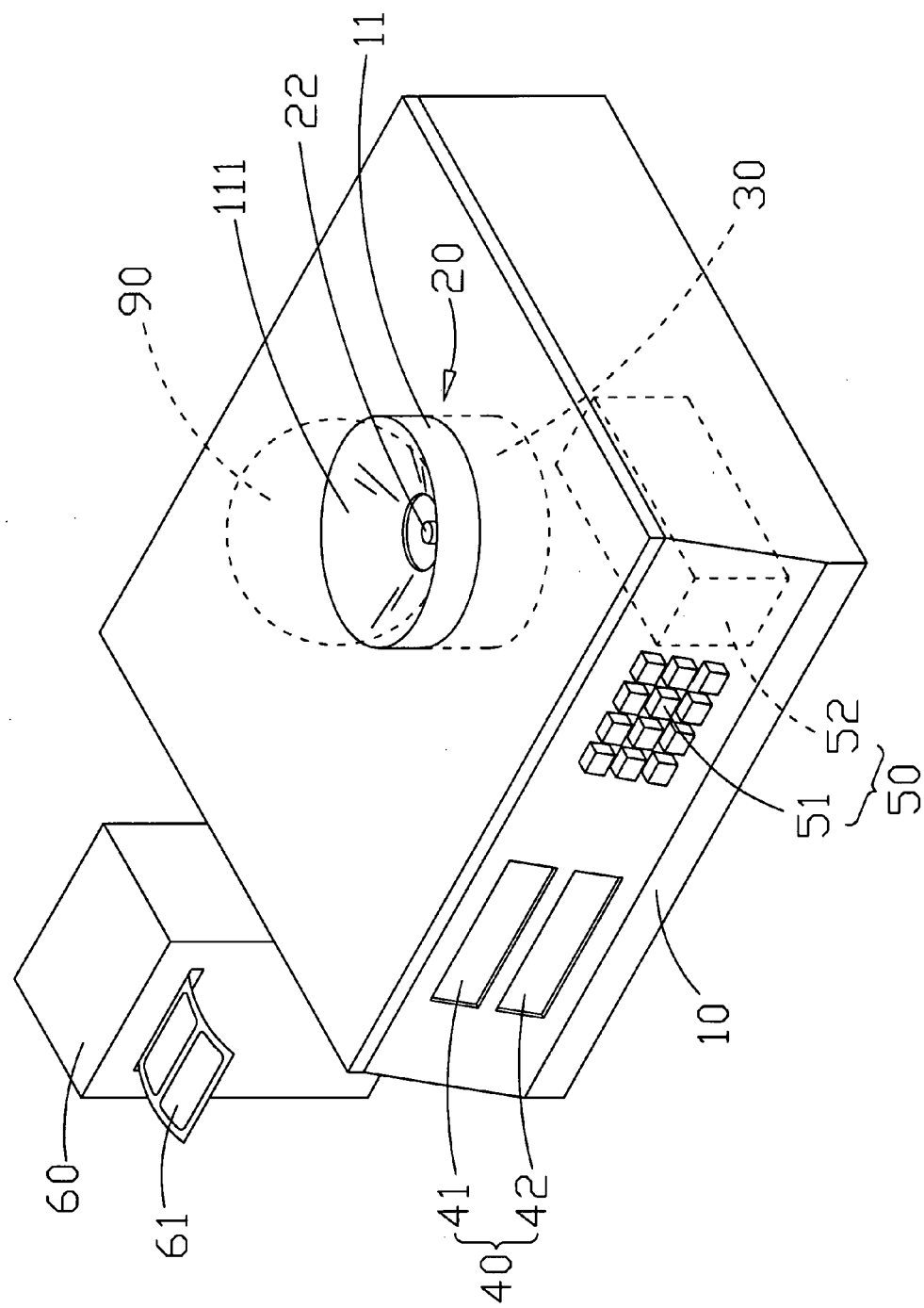
FIG. 1 is a perspective view showing a preferred embodiment of the present invention.

Referring to FIG. 1 showing a perspective view of a preferred embodiment of the present invention, an inspection instrument is comprised of a main unit 10, a Brix testing unit 20, a weight measurement unit 30, a display unit 40, a control unit 50 and a label printer 60. Wherein, the main unit 10 is related to a rigid enclosure; the Brix testing unit 20, the weight measurement unit 30, the display unit 40 and the control unit 50 are basically disposed on the main unit 10; and the control unit 50 is respectively linked to the Brix testing unit 20, the weight measurement unit 30, and the display unit 40. In the preferred embodiment, the label printer 60 is adapted to one side of the main unit 10; however, it may be integrated to the main unit 10 depending on the general design of the inspection instrument. The option is obvious to those who are familiar with the art of the present invention and thus will not be elaborated herein. Instead, only the operation relation between the label printer 60 and the inspection instrument will be described below. The label printer 60 is linked to the control unit 50 and directly prints the information (e.g., data of Brix or weight of the fruit tested) upon receiving it from the control unit 50 on a label 61, which is then outputted to be directly attached to the fruit inspected for achieving the purpose of real time inspection and record.

Figure 2:
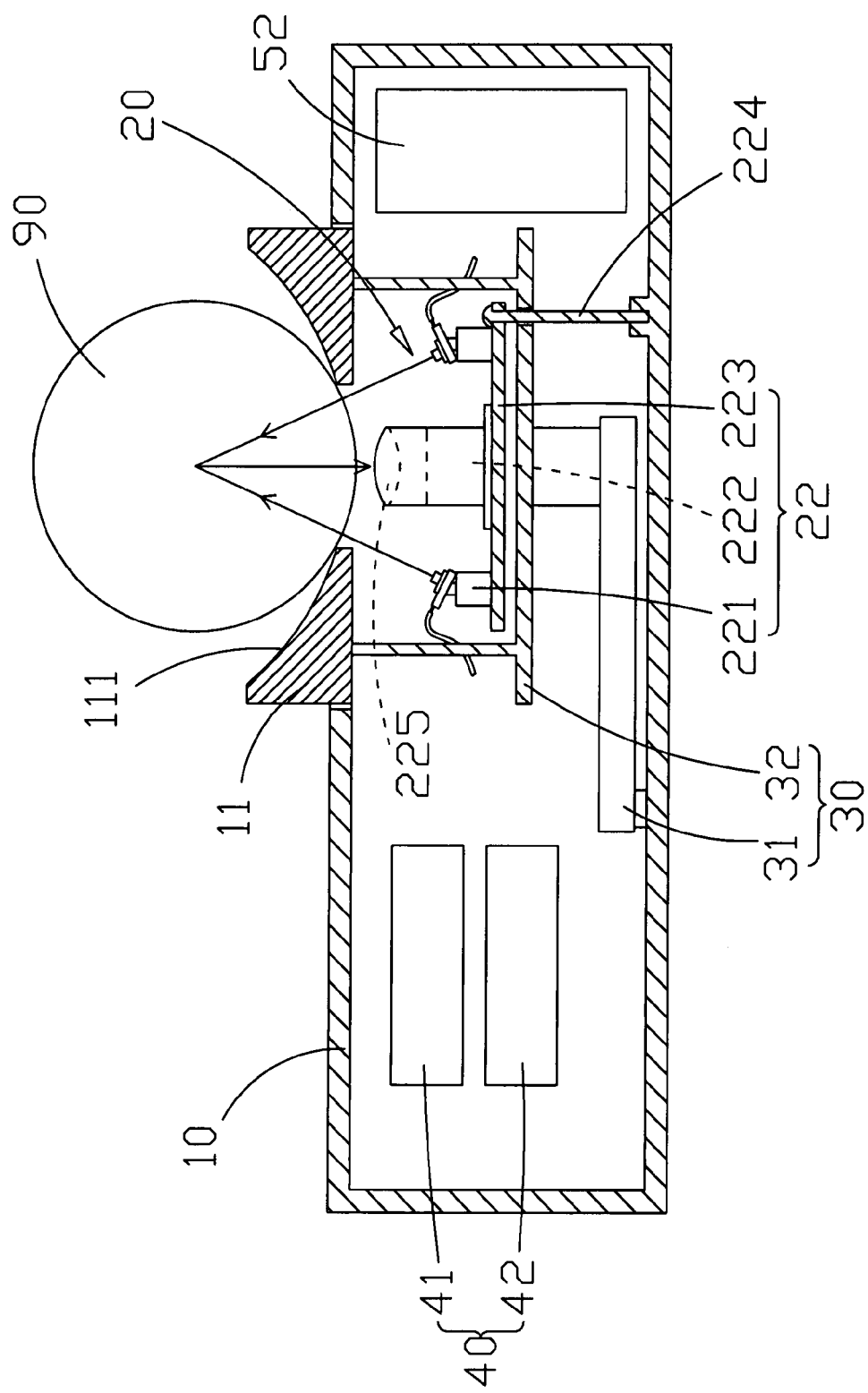
FIG. 2 is a sectional view showing the preferred embodiment of the present invention.

Now referring to FIG. 2 for a sectional view of the inspection instrument of the preferred embodiment, a holder 11 is further disposed to the main unit 10. The holder 11 is exposed out of the main unit 10 and contains a loading surface 111 for an object 90, e.g., fruit, pending test to be place thereon. The loading surface is made concave to facilitate securing the fruit in the holder 11, which is located at where above the Brix testing unit 20 and is secured to the weight measurement unit 30.

Figure 3:
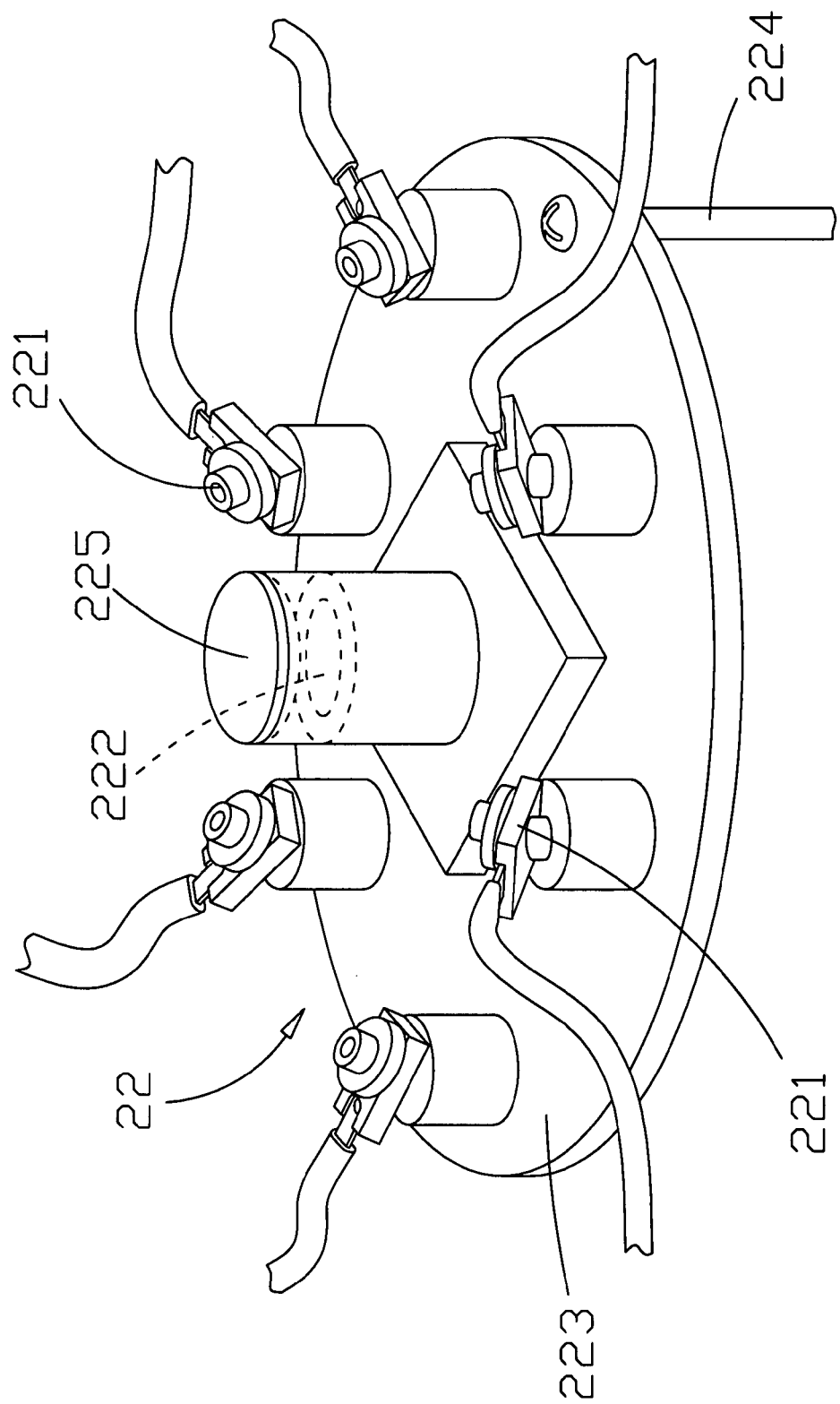
FIG. 3 is a perspective view showing a local part of a Brix testing unit in the present invention.

The Brix testing unit 20 is disposed in the main unit 10; and in the preferred embodiment, the Brix testing unit 20 is related to a laser testing component 22 to perform laser test upon the object 90 pending test. Located at where below the holder 11, the laser testing component 22 includes a laser transmission end 221, a laser receiving end 222, and a fixation disk 223; wherein, both of the laser transmission end 221 and the laser receiving end 222 are provided on the fixation disk 223, and the fixation disk 223 is fastened to a bottom of the main unit 10 with a bolt 224 so to keep the entire laser testing component 22 from contacting the holder 11 or the weight measurement unit 30 for preventing mutual interference. The laser receiving end 222 is located at a center of the holder 11. A convergence lens 225 is disposed on a top of the laser receiving end 222 to cope with the individual object 90 pending test by adjusting the convergence lens 225. The laser transmission end 221 is located by the laser receiving end 222 and six laser transmission ends 221 are disposed surrounding the receiving end 222 in the preferred embodiment as illustrated in FIG. 3 for a perspective view of a local part, i.e., the laser testing component 22, of the inspection instrument of the present invention. A laser diode disposed at each laser transmission end emits laser beams to enter into the object 90 pending test, signals transmitted from each laser transmission end is received by the laser receiving end 222 and then transmitted to the control unit, where signals converted into the ° Brix, after computation using mathematic formula. In the preferred embodiment, the ° Brix is expressed by numeric value, e.g., 10° Brix.

Figure 4:
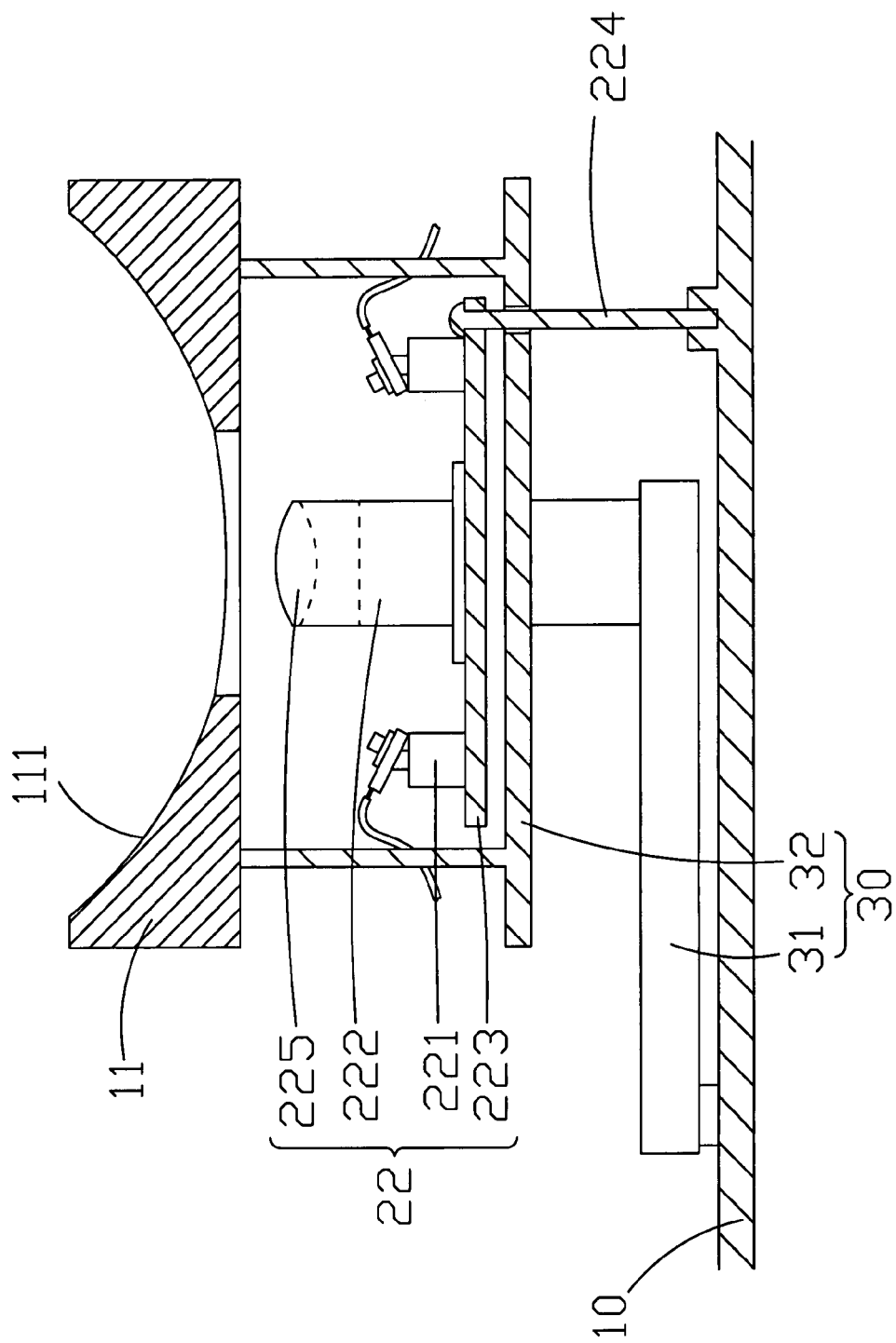
FIG. 4 is a perspective view showing a local part of a weight measurement unit in the present invention.

As illustrated in FIG. 4 for a perspective view showing the weight measurement unit of the present invention, the weight measurement unit 30 in the preferred embodiment contains a weight sensor 31 and a bracket 32 with the weight sensor suspended to the bottom of the main unit 10 and at where below the laser testing component 22. A center of the bracket 32 is fixed to the weight sensor 31 with one end holding against and connecting the holder 11. Whereas the entire weight measurement unit 30 does not directly contact the laser testing component 22, there will be no error created due to mutual affects between the weight measurement unit 30 and the laser testing component 22. With the object 90 pending test being placed on the holder 11, the holder 11 is subject to the weight of the object 90 pending test and thus to compress the weight sensor 31 for the weight sensor 31 to generate an electronic signal to be transmitted to the control unit 50 for solving the weight of the object 90 pending test.

As illustrated in FIGS. 2 and 3, the display unit 40 located on the main unit 10 to display information includes a first screen 41 and a second screen 42 to respectively display the Brix expressed in numeric value in the preferred embodiment, e.g., 10° Brix; and the weight, e.g., 1000.0 g or 0.1 kg.

The control unit 50 contains a control keypad 51 and a controller. The control keypad 51 is provided on the main unit 10 and linked to the controller 52 for keying in information of associate parameters to the controller 52 and for presetting each control key 51 to the parameter information adaptable to the individual object 90 pending test. A user presses different keys 51 according to the individual object 90 pending test to facilitate testing and measuring. The controller 52 is provided in the main unit 10 and is respectively linked to the Brix testing unit 20, the weight measurement unit 30, and the display unit 40 to receive or transmit related signals.

The inspection instrument of the present invention allows testing the Brix and measuring the weight of an object pending test at the same time (i.e., fruit) by operating the Brix testing unit 20 and the weight measurement unit 30; the resultant data are directly displayed on the display unit 40 mounted on the inspection instrument; then the resultant data (e.g., ° Brix or the weight of the fruit) are directly printed on a label and outputted for the label to be directly attached to the fruit in achieving the purpose of real time inspection and record.

Accordingly, an inspection instrument of the present invention for being capable of testing the Brix and measuring the weight of fruit at the same time, followed by immediate display of the resultant data to achieve precise control of the quality of each fruit and perform assorting by quality level in a non-destructive inspection method is innovative and advanced to meet requirements of patentability; therefore, this application is duly filed.

However, it is to be noted that the preferred embodiments disclosed in the specification and the accompanying drawings are not limiting the present invention; and that any construction, installation, or characteristics that is same or similar to that of the present invention should fall within the scope of the purposes and claims of the present invention.

We claim:

1. An inspection instrument comprising:
    a main unit;
    a Brix testing unit disposed in the main unit;
    a weight measurement unit disposed in the main unit and located below the Brix testing unit;
    a display unit disposed on the main unit; and
    a control unit provided with a control keypad and a controller, the control keypad being disposed on the main unit and linked to the controller, the controller being provided in the main unit and linked to the Brix testing unit, the weight measurement unit, and the display unit, respectively;
    wherein a holder is further disposed on and exposed out of the main unit and contains a loading surface, and the holder is located above the Brix testing unit and fixed to the weight measurement unit;
    wherein the Brix testing unit comprises a laser testing component comprised of a laser transmission end, a laser receiving end and a fixation disk, both of the laser transmission end and the laser receiving end being mounted on the fixation disk and the fixation disk being fastened to a bottom of the main unit; and
    wherein the weight measurement unit is comprised of a weight sensor suspended to the bottom of the main unit and below the Brix testing unit, and a bracket having its center fixed to the weight sensor and one end coupled to the holder, such that the Brix testing unit is free of physical contact with either of the weight measurement unit and the holder to allow the Brix testing unit and the weight measurement unit to operate independently from each other.

2. The inspection instrument as claimed in claim 1, wherein a label printer is provided to one side of the main unit and is linked to the control unit.

3. The inspection instrument as claimed in claim 1, wherein the fixation disk is fastened to a bottom of the main unit with a bolt.

4. The inspection instrument as claimed in claim 3, wherein the laser receiving end is located in registration with a central portion of the holder, and the laser transmission end is located lateral to the laser receiving end.

5. The inspection instrument as claimed in claim 3, wherein a convergence lens is disposed on a top of the laser receiving end.

6. The inspection instrument as claimed in claim 1, wherein the display unit is comprised of a first screen and a second screen; the first screen displays a value of Brix; and the second screen displays a value of weight.

7. The inspection instrument as claimed in claim 1, wherein the laser transmission end is provided with a laser diode.

* * * * *